United States Patent [19]

Chenchik et al.

[11] Patent Number: 5,665,544

[45] Date of Patent: Sep. 9, 1997

[54] RNA FINGERPRINTING TO DETERMINE RNA POPULATION DIFFERENCES

[75] Inventors: Alexander Anatoljevich Chenchik; Ludmila Borisovna Diachenko; Robert Shavlovich Beabealashvili, all of Moscow, Russian Federation; Christopher John Carter, Amersham, England

[73] Assignee: Amersham International plc, Buckinghamshire, England

[21] Appl. No.: 343,449

[22] PCT Filed: May 27, 1993

[86] PCT No.: PCT/GB93/01102

§ 371 Date: Jun. 9, 1995

§ 102(e) Date: Jun. 9, 1995

[87] PCT Pub. No.: WO93/24655

PCT Pub. Date: Dec. 9, 1993

[30] Foreign Application Priority Data

May 27, 1992 [GB] United Kingdom ............ 92304790

[51] Int. Cl.[6] .................................................. C12Q 1/68
[52] U.S. Cl. .................................. 435/6; 935/77; 935/80
[58] Field of Search .............................. 435/6, 5; 536/24.3; 935/77, 80

[56] References Cited

FOREIGN PATENT DOCUMENTS 63-241356 10/1988 Japan .................... G01N 33/50
WO9105064 4/1991 WIPO .
WO9114001 9/1991 WIPO .
WO9203567 3/1992 WIPO .
WO9207095 4/1992 WIPO .

OTHER PUBLICATIONS

Chenchik et al. (1993) *FEBS Letters* 321:98–101.
Chenchik et al. (1993) *FEBS Letters* 324:136–9.
Zimmern and Kaesberg (1978) *Proc. Natl. Acad. Sci. USA* 75:4257–61.
Palmenberg et al. (1984) *Nucleic Acids Res.* 12:2969–85.
Langer et al. (1981) *Proc. Natl. Acad. Sci. USA* 78:6633–37.
Rosemeyer et al. (1995) *Anal. Biochem.* 224:446–9.
Liang and Pardee (1992) *Science* 257:967–71.
Yamaguchi and Saneyoshi (1995) *Nucleic Acids Symposium Series* No. 34, pp. 75–76.
Hamlyn et al. (1977) *Nucleic Acids Res.* 4:1123–34.
Efremov et al. (1991) *Hemoglobin* 15:525–33.
Welsh et al. (1992) *Nucleic Acids Res.* 20:4965–70.
R.C. Mierendorf et al., Methods in Enzymology, vol. 152, New York (1987), pp. 563 to 566.

*Primary Examiner*—W. Gary Jones
*Assistant Examiner*—Amy Atzel
*Attorney, Agent, or Firm*—Wenderoth, Lind & Ponack

[57] ABSTRACT

A method of producing an RNA fingerprint of a poly(A)[+] RNA preparation. At least one oligonucleotide primer and a supply of nucleotides of which one is a terminator nucleotide, are added to the poly(A)[+]RNA preparation or a single-stranded cDNA preparation derived from it. cDNA products are synthesized from the RNA, or DNA products from the cDNA and the products are separated to produce an RNA fingerprint.

12 Claims, 6 Drawing Sheets

RNA FINGERPRINTING TO DETERMINE RNA POPULATION DIFFERENCES

BACKGROUND TO THE INVENTION

The total number of expressing genes in a typical mammalian cell is unknown, although current estimates range from 10000 to 20000 (1, 2). As many as 70–90% of these genes may perform 'household' functions and are likely to always be expressed by different cell types irrespective of their origin (2). In total, there are perhaps 50000–100000 genes expressed in all the different cell types from a given mammal, based on the fact that approximately 3% of the haploid genome corresponds to genes (2).

High resolution 2-dimensional protein gel electrophoresis is commonly used for visualising large numbers of individual gene products expressed simultaneously in a given cell type. At present, the sensitivity of most available 2-dimensional gel techniques limits their use to providing quantitative (and qualitative) analysis of only those 1000–2000 proteins that comprise more than 0.001% of the total protein from a typical mammalian cell type (3). This approach may, however, allow the identification of phenotype specific proteins, involved, for example, in human disease, carcinogenesis, cell differentiation, proliferation and ageing, which can then be microsequenced to provide information so that cDNAs coding for such proteins can eventually be isolated (4).

Unfortunately, to date, an efficient, well developed technique for determining differences in poly(A)$^+$RNA composition and for monitoring changes in gene activity by the simultaneous quantitative and qualitative analysis of several hundred individual mRNAs has not been available. The use of a technique based on RNA analysis would not only generate additional information, to complement that obtained using 2 dimensional protein analysis, but would also provide a more convenient means for the cloning/ sequencing of differentially expressed genes. RNA transcripts of DNA can be sequenced using suitable primers, in chain termination reactions (Mierendorf et al, Methods in Enzymology (1987) 152, 563–566). For the past 15 years, differential screening of cDNA libraries has been widely applied for the isolation of differentially expressed genes (5,6). This technique is, however, rather inefficient and labour intensive, requiring several hundred micrograms of poly(A)$^+$RNA and several months work to isolate a small number of useful cDNA clones (7). Also, the use of 'enriched' cDNA probes/libraries or the application of PCR technology for amplification of such libraries only partially solves the problem of cloning low abundance, differentially expressed, cDNAs (8). Amplification of DNA/cDNA using PCR, with pairs of arbitrary sequence primers (18–40 nucleotides in length), has been used for the identification and characterization of mutations, resulting from nucleotide substitutions, insertions or deletions (9) or for the analysis of cDNA composition differences (9–11). However, this revealed only qualitative, rather than quantititative differences between two different RNA populations. This was mainly because short (8–10 nucleotide) primers, when used for cDNA analysis, are relatively inefficient in the PCR process (9), and the degree of amplification is also more sensitive to both the primary structure of the template DNA and to the reaction conditions used (12). Described herein is a new method for determination of the poly(A)$^+$RNA composition (pattern) of a given cell or tissue type.

SUMMARY OF THE INVENTION

The present invention provides a method of producing an RNA fingerprint of a poly(A)$^+$RNA preparation, comprising adding to the poly(A)$^+$RNA preparation at least one oligonucleotide primer and a supply of nucleotides of which one is a terminator nucleotide, synthesising cDNA products from the RNA template and separating the cDNA products to produce an RNA fingerprint. In another approach, this invention can be used to obtain a similar fingerprint by utilizing single-stranded cDNA, transcribed from the poly(A)$^+$RNA, as the template in the above process.

An RNA fingerprint is therefore defined herein as a pattern or array of small DNA products, specific to a particular preparation of poly(A)$^+$RNA, or its cDNA product, processed according to the described method in combination with a particular set of primers.

The oligonucleotide primers are preferably DNA primers between 8 and 10 nucleotides in length and most preferably 9 nucleotides in length. The number or sequence of the oligonucleotides primers used is not critical to the invention. The number of different primers used is preferably chosen to provide a sufficiently detailed RNA fingerprint to allow it to be distinguished from the RNA fingerprints of different RNA preparations as required. The sequence(s) of the primer(s) may also be chosen to achieve the above end.

The terminator nucleotide could be any terminating nucleotide, in particular any dideoxynucleoside triphosphate ddNTP (i.e. any one of ddATP, ddCTP, ddGTP, ddTTP or ddUTP, but is preferably chosen as dideoxyuridine triphosphate ddUTP. The ddUTP is also preferred to contain a fluorescein or biotin residue, in the form of ddUTP (5AA-FAM) or ddUTP (5AA-Bio), although this is not critical to the invention.

It is also preferred that the separating of the cDNA or DNA products is carried out by electrophoresis.

In the method of the invention, the oligonucleotide primer may be labelled with a detectable label. Alternatively or additionally, a ddNTP terminator used in the method could be labelled with a detectable label. Suitable labels may be radioactive or fluorescent species or other non-radioactive labels used in conjunction with appropriate detection systems known in the art.

DETAILED DESCRIPTION OF THE INVENTION

The invention is suitable for analyzing and comparing the relative amounts of several hundred of the more abundant individual mRNAs present in different poly(A)$^+$RNA preparations. The method, as carried out in the Examples presented here, is based on the synthesis of short cDNA products, by reverse transcription of poly(A)$^+$RNA, primed with a 5'-labelled oligonucleotide. Three natural nucleotides and one terminator nucleotide are used as substrates for this reverse transcriptase reaction. A number of different oligonucleotides are used as primers in separate reactions, their length and sequences having been chosen to provide more than a 90% probability of initiating synthesis from any individual RNA present in the poly(A)$^+$RNA. This provides a comprehensive analysis of all RNAs having abundances higher than 0.1%. Each primer produces about 10–60 bands per track following polyacrylamide gel (PAAG) electrophoresis under denaturing conditions. If the full set of 30 oligonucleotides described herein is used to analyse a poly (A)$^+$RNA preparation, an electrophoretic pattern can be obtained which provides information similar to that given by high resolution 2-dimensional protein gel electrophoresis. Data presented reveals poly(A)$^+$RNA/cDNA pattern differences for a number of human tissues from several individuals and identifies changes in the RNA patterns between normal tissues and neoplastic human tumors (myoma of the uterus) and also during differentiation of F9 fetal carcinoma cells. The direct chemical sequencing of specific bands excised from the resulting polyacrylamide gel can provide enough information for the identification of differentially expressed genes in the GeneBank database. This information can then be used to allow direct primer extension sequencing of poly(A)+RNA (13), PCR amplification/ cloning (9,10) and identification of differentially expressed genes from a cDNA library using a hybridization approach.

The following Examples illustrate the invention. The field of application of the method is shown in various models by analyzing the differences in the pattern of poly(A)+RNAs from different tissues (normal and transformed tissues) and by monitoring the changes of poly(A)+RNA patterns during F9 cell differentiation.

EXAMPLES

MATERIALS AND METHODS

Synthesis and purification of oligonucleotides
Oligonucleotides:

| | | |
|---|---|---|
| F1 (TGCAGGCTG), | F2 (TGCAGGTGG), | F4 (TGGAGCTGG), |
| F2 (TGTGGCTGG), | F6 (TGTGGCAGG), | P8 (TGCTGGGGA), |
| P10 (TGCTGGAGG), | P32 (TGCTGGAGT), | P33 (TGCTGGACG), |
| P34 (TGCTGGATG), | P35 (TGCTGGCGG), | P36 (TGCTGGTGG), |
| P37 (TGCTGCAGG), | P38 (TGCTGTAGG), | P39 (TGCTGGCGT), |
| P40 (TGCTGGCGC), | P41 (TGCTGGCAG), | P42 (TGCTGGCCG), |
| P43 (TGCTGACGG), | P44 (TGCTGTCGG), | P46 (TGCTGGTGT), |
| P47 (TGCTGGTGC), | P48 (TGCTGGTAG), | P49 (TGCTGGTCG), |
| P50 (TGCTGGCGA), | P51 (TGCTGGTGA), | P55 (TGCTGGGTG), |
| P56 (TGCTGGTTG), | P57 (TGCTGGCTG), | P59 (TGCTGCATG) | were synthesized on a 370A DNA synthesizer from "Applied Biosystems" and purified by 20% PAAG-urea gel electrophoresis. Oligonucleotides were labelled using [gamma-$^{32}$P]ATP ("Amersham") and T4 polynucleotide kinase in accordance with (14).

Poly(A)+RNA purification

All normal tissues and cirrhotic liver were obtained within 1–2 hours of sudden death and stored at −70° C. Cirrhotic liver was characterized by a higher percentage (40±13%) of micronodular tissue in comparison with normal liver (3±1%). Myometrium (without endometrium impurities) and myoma nodules were obtained at the time of uterus ablation from three patients. Leomyoma of the uterus was diagnosed histologically for all three cases in accordance with classification (15). The F9 embryonal carcinoma cells were maintained in the undifferentiated state in DMEM, 10% fetal calf serum, 100 units/ml penicillin, 100 units/ml streptomycin in gelatin-coated tissue culture flasks. The F9 cells were induced to differentiate by treatment with 0.2 uM all-trans retinoic acid and 1 mM dibutyryl cAMP and collected as described by Strickland et al (16).

Total RNAs were purified from frozen tissues (cells) using the guanidine thiocyanate/phenol chloroform extraction method as described by Sambrook J. et al (17). The 28S:18S RNA ratio was at least 2:1 for all preparations of total RNAs, as determined by agarose-glyoxal gel electrophoresis (17).

Poly(A)+RNAs were purified from total RNAs by two rounds of oligo-d(T)-cellulose chromatography (17).

cDNA synthesis and electrophoretic separation of products a) 5′-[$^{32}$P]-labelled primer 0.2 pmol 5′-[$^{32}$P]-labelled primer was annealed with 0.02–0.2 μg of poly(A)+RNA or single-stranded cDNA template, in 1 μl of deionized water, by heating for 2 min at 95° C., followed by incubation for 10 to 20 minutes at 25° C. cDNA synthesis initiated by mixing the annealed primer-RNA and 20 units of M-MLV reverse transcriptase ("Gibco-BRL") in a final volume of 2 μl, containing 50 mM Tris-HCl (pH 8.3 at 22° C.), 75 mM KCl, 3 mM MgCl$_2$, 1 mM DTT, 50 μg/ml BSA, 20 μM each of dATP, dGTP, dCTP and 50 μM ddUTP (5AA-Fam), modified by a fluorescent (Fam) or biotin (Bio) residue at the 5-position of the uridine base (18). After 12 hours at 42° C., 200 μg/ml of snake venom phospodiesterase ("Pharmacia") and 100 mM glycine NaOH, pH 10.1, were added and then incubated for 45 min at 56° C. The phosphodiesterase reaction was stopped by addition of 2 μl of 95% formamide, 10 mM EDTA, pH 8.0, then heated for 2 min at 95° C. One half of the sample was then subjected to electrophoresis through a 20% polyacrylamide gel (19:1 monomer to bis), containing 7 M urea buffered with 0.1M Tris-borate, pH 8.5, 1 mM EDTA. Electrophoretic separation of samples was performed at constant current (25 mA) and constant temperature (55° C.). Oligo d(T)$_n$ was used as a size marker on the gel.

b) [$^{32}$P]-labelled terminator

Annealing of template with unlabelled primer, and cDNA synthesis conditions were identical to those described using the 5′-[$^{32}$P] labelled primer except that the concentrations of dGTP, dCTP and dTTP used were 5 μM, and the [$^{32}$P]-labelled terminator, ddATP (100 Ci/mmol) was present at 10 μM. The phosphodiesterase step was not required when using this method, but the cDNA synthesis reaction was stopped by adding formamide and the reaction mix was then analysed by polyacrylamide gel electrophoresis, as described under (a).

Preparation of single-stranded cDNA template

Single-stranded cDNA was synthesised using a 5′ biotinylated F6 primer and 10 μg of poly(A)+RNA in a 100 μl reaction volume, under the reaction conditions described in the cDNA synthesis section (a) but without the terminator nucleotide and with all four normal dNTPs, each present at 500 μM. Following the synthesis reaction, 10 μl of 1M NaOH, 100 mM EDTA solution was added and the reaction mix was incubated at 65° C. for 45 minutes. The pH was then adjusted to between 7 and 8 by adding 12 μl of 1M HCl, followed by the addition of 15 μl of 100 mM Tris-HCl, pH 7.5, 2.5M NaCl, 0.5% N-lauroyl sarcosine, 5 mM EDTA and finally 15 μl of 5M guanidinium thiocyanate, before heating at 95° C. for 5 minutes. The biotinylated cDNA products were bound to 200 μl of Streptavidin-agarose ("Sigma") at 25° C. for 20 minutes, washed, twice with 0.5 ml of 10 mM NaOH and then twice with 0.5 ml of 20 mM Tris-HCl, pH 7.5, 0.5M NaCl, 0.1% N-lauroyl sarcosine, 1 mM EDTA before eluting with 50 μl of 5M guanidium thiocyanate at 95° C. for 5 minutes. The cDNA was then further purified by gel filtration, using a 1 ml Sephadex™ G100 column, and concentrated by ethanol precipitation.

Chemical sequencing of oligonucleotides

Bands were excised from the gel and oligonucleotides were eluted by incubating each gel slice for 3 hr at 55° C., in 1 ml of deionized water containing 5 μg/ml of total yeast RNA. Each solution was then loaded onto a DE52 cellulose column (5 μl), and the oligonucleotide was eluted in 20 μl of 1M NaCl, desalted on a G15 sephadex™ column (200 μl) equilibrated with deionized water, and dried under vacuum. Cleavage at G residues with dimethylsulphate, G+A residues with piperidinium formate and T residues with potassium permanganate were carried out as described (19). The reaction on C residues was performed with hydrogen peroxide (20). Piperidine strand cleavage was used for all reactions (19). Electrophoresis of the cleavage products was performed using a 20% polyacrylamide-urea gel.

Searching for mRNA target sites

We have used the Wisconsin University GCG computer programme (21) and the GeneBank (release 70.0) database to identify sequences complementary to the sequenced oligonucleotides.

RESULTS AND DISCUSSION

General description of the poly(A)⁺RNA pattern method

The poly(A)⁺RNA pattern method, described here in the examples, is based on quantitative and qualitative analysis of cDNA products synthesized by M-MLV reverse transcriptase using poly(A)⁺RNA as a template, a set of 5'-end labelled primers (9 nucleotides long), and 3 natural deoxyribonucleotides (dATP, dGTP, dCTP) with 1 terminator ddUTP(5AA-Fam) or ddUTP (5AA-Bio). Under the conditions used (see "Materials and methods" section) at least 98% of synthesized products were terminated at the first T in the growing chains. After the synthesis stage, all non-terminated products and the remaining primers can be selectively removed by hydrolysis, following treatment with snake venom phosphodiesterase. The 5'- modified analogue of ddUTP was chosen as the terminator, since extension products containing a 3'- ddUMP(5AA-Fam) or ddUMP (5AA Bio) are at least 100 fold more resistant to the action of snake venom phosphodiesterase than the corresponding non-terminated oligonucleotides (22). This phosphodiesterase step is performed to reduce the "background" contributed by any unreacted primers/non terminated products, although it is not an essential part of the invention. Using a labelled terminator [$^{32}$P]ddATP ("Amersham"), instead of a 5'-[$^{32}$P]-labelled primer, enables the phosphodiesterose step to be avoided, since only terminated products will appear labelled on the subsequent autoradiograph.

The 3'-terminated oligonucleotides (10–30 nucleotides long), were separated using 20% polyacrylamide gel electrophoresis, under denaturing conditions, where migration of the DNA fragments was dependent on both their length and the primary structure of their 3' ends (23). The electrophoretic conditions employed allowed the resolution of up to 60 bands per track (1 primer) for oligonucleotides of 10–30 nucleotides in length. The presence of the bulky hydrophobic Fam (Bio) residue attached to the uridine base in oligonucleotides terminated with the ddUMP analogue resulted in these molecules migrating as if they were 2 nucleotides longer than non-terminated oligonucleotides of the same length. The primary structures of all primers mentioned were selected using the following criteria. All oligonucleotides were synthesized in accordance with results of computer analysis of the most commonly used sequences in the coding regions of 200 mammalian genes. Lengths and sequences of primers were selected so that the probability of two complementary sequences appearing in any individual mRNA wouldn't exceed 3%. Any repetitive, palindromic and homopolymeric sequences were minimised by using the algorithm developed by Sieminick et al (24). The sequences of the primers were chosen to maximize the specificity of binding to the complementary template sequence and minimize binding to secondary non-complementary sites during subsequent cDNA synthesis. The optimum design of primers was developed on the basis of results from cDNA synthesis primed using completely and partially complementary primers with T7 RNA polymerase synthesized template RNA. Under the conditions used to generate poly(A)⁺RNA patterns, the ratio of complementary to non-complementary cDNA synthesis for all primers used was at least 10:1. The molar concentration of primer was at least equal to, or greater than, the concentration of any individual RNA in the poly(A)⁺RNA population.

Example 1

Comparison of the poly(A)⁺RNA pattern for different normal human tissues

Figure 1:
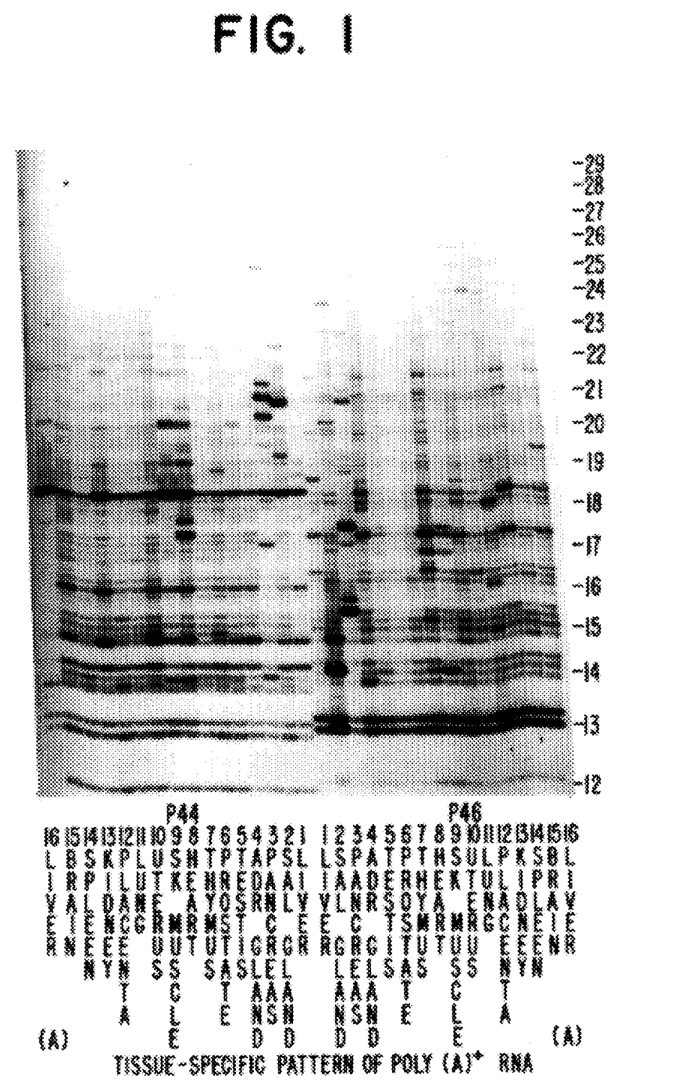
FIG. 1 Poly(A)$^+$RNA pattern of terminated cDNA synthesis products catalyzed by M-MLV reverse transcriptase on human poly(A)$^+$RNAs (1–15) or poly(A)$^-$RNA (16) using primers P44 or P46. M=oligo-d(T)$_n$ size markers, n=12, 13, 14 etc. Brackets show the width of distribution of electrophoretic mobilities for terminated oligos with the length of 11, 12, 13, 14 etc.

FIG. 1 shows the differences in electrophoretic pattern of cDNA products synthesized by M-MLV reverse transcriptase from poly(A)⁺RNAs purified from 15 different human tissues (lanes 1–15) or poly(A)⁻RNA (lane 16) used as templates, and with 5'-labelled oligo P44 or P46 used as primers. The electrophoretic patterns obtained are very reproducible and unique for each poly(A)⁺RNA when any of the oligonucleotides, listed in the "Materials and Methods" section, are used as the primer. Poly(A)⁺RNA patterns from histologically different tissues (for example, from liver (lane 1) and brain (lane 15)) possess more differences than poly (A)⁺RNAs from similar tissues (for example, skeletal muscle (lane 9), heart (lane 8) and uterus (lane 10)). The poly(A)⁻RNA pattern (lane 16) is not as complicated (oligo P44) as those patterns obtained using poly(A)⁺RNAs (lanes 1–15), or is characterized by an absence of any bands (oligo P46). As with P44 and P46, all the other primers used produce very simple poly(A)⁻RNA patterns which are also independent of the tissue origin of the template poly(A)⁻ RNAs (data not shown). The same pattern was obtained using different concentrations (10–200 µg/ml) of poly(A)⁺ RNA in the reaction mixture. Using 10 µg/ml of poly(A)⁺ RNA, produced band intensities as shown in FIG. 1 (when using an overnight exposure with an intensifying screen). Adding a different quantity of T7 RNA polymerase synthesised template RNAs to the liver poly(A)⁺RNA, we have shown that the intensities of the newly synthesised bands are proprotional to the amount of added T7 RNA polymerase synthesised RNA templates, when these are in the 0.1%–20% abundance range. Quantitative comparisons between different poly(A)⁺RNAs for a given mRNA/primer product will therefore be valid providing the gel band contains only one specific product. Based on these data, we estimate that the most intense signals (for example in lane 2 with primer P46) correspond to about 0.05 µM individual mRNAs (5% of poly(A)⁺RNA) whilst the least intense signals correspond to abundance levels of 0.01%–0.05% of individual RNAs in poly(A)⁺RNA preparations (primer P46, lane 6, bands longer than 11 nucleotides). The strongest signals commonly correspond to poly(A)⁺RNAs purified from tissues overproducing specific proteins (for example glands: pancreas (lane 3), salivary (lane 2), adrenal (lane 4), liver (lane 1), and muscle tissues: heart (lane 8), Skeletal muscle (lane 9) and uterus (lane 10)). It has been shown that the content of individual mRNAs coding for tissue-specific proteins in such tissues can reach (20–30%) (1, 2).

The presence of strong secondary structure in the mRNA at the site of primer-template interaction can reduce the level of cDNA synthesis and affect the corresponding band intensities on the gel. The adverse effects of mRNA secondary structure could be minimised by performing cDNA synthesis at an elevated temperature, using a thermostable DNA polymerase, such as Tth or TetZ, which also possesses thermostable reverse transcriptase activity. This would tend to even out band intensities for target molecules of equivalent concentrations. These band intensities also depend on primary structure of the oligonucleotide primer, but to a lesser extent. The main effects (3–5 fold) on band intensities are observed when using primers, containing purine-rich or pyrimidine-rich sequences at their 3'-ends. Dependence of the average band intensities on the length of the terminated products is also difficult to predict since phosphodiesterase action is not fully blocked by the presence of a terminator nucleotide ddUMP(5AA-Fam) at the 3'-oligo end (22). The residual rate of hydrolysis of a terminated oligo depends on both its length and the primary structure of its 3'-ends, and it appears that shorter oligos are hydrolysed more rapidly, leading to a proportionately greater reduction in the intensities of these bands. Small impurities of dTTP in the dNTP preparation used may also lead to the appearance of additional bands, usually 50–100 times less intense than the main band for many mRNAs, and their presence may contribute to the intensities of the longer oligo bands.

Figure 2:
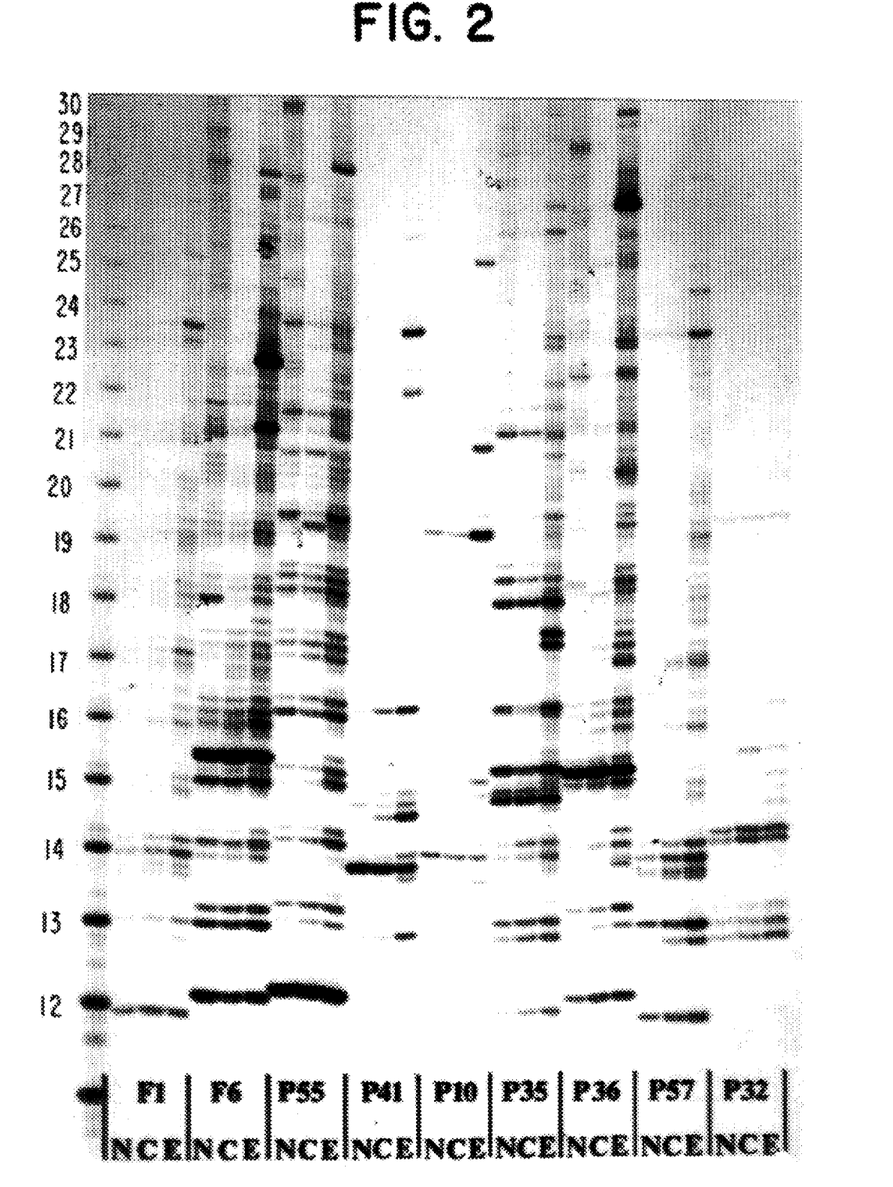
FIG. 2 Comparison of poly(A)$^+$RNA patterns for normal (N), cirrhotic (C) and fetal (E) human livers using the primers F1, F6, P55, P41, P10, P35, P57, P32.

The quantity of bands present in each lane is partly determined by the complexity of the poly(A)⁺RNA population and also by the primary structure of the oligo primer used. The simplest pattern of cDNA synthesis products is typical for RNAs with low complexity (e.g. poly(A)⁻RNA (lane 16) and poly(A)⁺RNA from some glands: pancreas (lane 9) and liver (lane 1)). Increasing the complexity of poly(A)⁺RNA leads to the appearance of a greater number of bands per lane—see brain (lane 15), spleen (lane 14). The primary structure of oligos and their length are, however, still the main factors that determine the number of bands in the electrophoretic pattern. At least a 10-fold change in the number of bands can be achieved by a a single nucleotide substitution around the 3'-end of the primer (FIG. 2) or by changing its length by a single nucleotide (data not shown). Obviously, the influence of the primary structure of the primer on the quantity of bands is dependent upon both the frequency of appearance of complementary sequences in the template RNA and the efficiency of cDNA synthesis from mismatched primer-RNA heteroduplexes (25).

In order to interpret the information obtained from the banding pattern we can consider bands corresponding to particular oligo sizes. For example, lane 15 (oligo P46), FIG. 1, the sequence, of length 10 nucleotides terminated at the first T is pTGCTGGTGTT* (T*=terminator ddUMP(5AA-Fam)) and has a mobility similar to d(T)$_{12}$. Assuming that 50 different mRNAs in the poly(A)⁺RNA (brain) can be used as templates for the P46 primer, then about 50 different terminated oligos can be synthesized from the P46 primer on this poly(A)⁺RNA. Approximately 25% of all these synthesized products (derived from about 12 individual RNAs) should therefore give only 1 band with the same 10 nucleotide long sequence. Analysis of the individual intensities of each of these 10 nucleotide terminated oligos is however impossible because they co-migrate. A group of bands with the length of 11 nucleotides and mobilities similar to d(T)$_{13}$ have the following structures: pTGCTGGTGTCT*, pTGCTGGTG-TAT* and pTGCTGGTGTGT* (order corresponds to the decreasing mobility of these oligos in the gel) and all three can be detected when using primer P32 (lane 1, 2, and 3), FIG. 2. However, oligo pTGCTGGTGTGT* is not observed when using primer P46 (FIG. 1). There are 9 theoretically possible terminated oligos with a length of 12 nucleotides with the following sequences: pTGCTGGTGTCCT*, pTGCTGGTGTACT*, pTGCTGGTGTCAT*, pTGCTGGTGTAAT*, pTGCTGGTGTCGT*, pTGCTGGTGTGCT*, pTGCTGGTGTAGT*, pTGCTG-GTGTGAT* and pTGCTGGTGTGGT*. These generate from 3 (P46) to 5 (P44, lane 5) distinguishable bands in the 12 nucleotide zone in FIG. 1 suggesting the possible coincidence of mobilities of different oligos and highlighting the very complicated dependence of mobility on the 3'-terminal nucleotide sequence (23). The different number of bands in the zone for 12 nucleotide long oligos, may also mean that not all possible terminated oligos exist in these cDNA synthesis products. Since several oligos appear to correspond to each band in this zone, it may prove difficult, using the present separation system, to correlate specific oligonucleotide sequences of 12 nucleotides or more with individual bands on the gel.

The number of bands registered on FIG. 1 for poly(A)⁺ RNA from a number of tissues are in the range of 10–60, although the real number of terminated oligos is probably several fold more. The number of different primers required for an extensive analysis of individual RNA species present in poly(A)⁺RNA preparations was determined as follows. The number of individual RNAs having an abundance of more than 0.1% (the detection limit of the poly(A)⁺RNA pattern method) of poly(A)⁺RNA ranges from 100 to 500 (1, 2). The fraction of poly(A)⁺RNA used as a template for cDNA synthesis for a set of individual primers has been determined and was found to vary between 0.5% to 30%, depending on the primer used (26). The set of 30 primers (see "Materials and Methods" section) allows the analysis of approximately 90% of all the RNAs in liver poly(A)⁺RNA within the detection limit (>0.1% abundance), using only 1 μg of poly(A)⁺RNA in total for all primer reactions.

Example 2

Comparison of normal, cirrhotic and fetal livers

To demonstrate further the application of the poly(A)⁺ RNA pattern method we investigated the differences in the poly(A)⁺RNA spectra from three morphologically and functionally similar tissues: normal, cirrhotic and fetal livers. Of the 30 primers used, at least 28 showed clear quantitative or qualitative differences in individual RNA pattern from normal and fetal liver poly(A)⁺RNA, but only 5 primers produced different poly(A)⁺RNA spectra for normal and cirrhotic livers. The data shown in FIG. 2 demonstrate such differences in the poly(A)⁺RNA spectra for normal and embryonal livers (primer F1, F6, P55, P41, P10, P35, P36, P57), and for normal and cirrhotic livers (F6, bands 1, 2; P55, band 3; P35, band 4; P36, bands 5, 6; P57, band 7) with no such differences observed for primer P32. The poly(A) ⁺RNA pattern method therefore allows us to identify differences in poly(A)⁺RNA spectra from similar tissues. Attempts to correlate any changes in poly(A)⁺RNA spectra with the pathology of cirrhosis are not yet possible using this technique, as is also the case with two-dimensional protein gel electrophoresis (3). It is essential to demonstrate if the differences observed result from individual (patient) differences in gene expression or by the pathogenic mechanism. Changes in poly(A)⁺RNA spectra in liver may also be due to decreasing the proportion of hepatocytes and increasing the proportion of connective tissue (27). All differentially represented bands (FIG. 1) did not show individual-specific differences although six primers out of 30 primers tested revealed individual-specific differences (about 0.2% of total number of bands in poly(A)⁺RNA pattern) (data not shown). To prove that the observed differences in the poly(A)⁺RNA spectra reflect differences in the poly(A)⁺RNA composition, we isolated and sequenced several arbitrarily chosen bands 8–18. Table 1A shows the sequences of these bands and the results of searching for possible complementary sequences in the GenBank database. Out of 11 sequences analyzed, 2 sequences (bands 14, 15) did not correspond to any sequence desposited in the GenBank database. For the remaining 7 sequences (bands 9, 10, 11, 12, 13, 17, 18), a unique complementary sequence was found. One sequence (band 16) corresponded to two target individual mRNAs and there were a number of mRNAs (6 human genes) which possessed a complementary target site for the sequence of band 8. In accordance with data shown in table 1A and FIG. 1, α1-globin, α2-globin, Ay-globin, Gy-globin and insulin-like growth factor mRNAs apparently exhibit enhanced expression in fetal liver compared with normal liver. This is in accordance with numerous data concerning enhanced expression of these genes during fetal development (28, 29). Mismatch analysis shows that the allowed mismatches are located within the first four nucleotides at the 5'-end of the primer (table 1).

Example 3

Myoma of the uterus

In order to answer questions about the significance of individual differences in poly(A)$^+$RNA spectra and possible linkage of pattern changes with pathology, we have chosen to study the model of human myoma of the uterus, which seems ideal for the following reasons.

1. Myoma of the uterus is a very widespread oncological disease, so it is possible to obtain statistically reliable data using multiple samples.

2. Normal myometrium consists of an homogeneous population of smooth-muscle cells (98%) and myoma is characterized by the appearance of only one type of cell (15).

3. Normal myometrium surrounding the myoma could serve as an internal control to myoma, without any individual differences.

Figure 3:
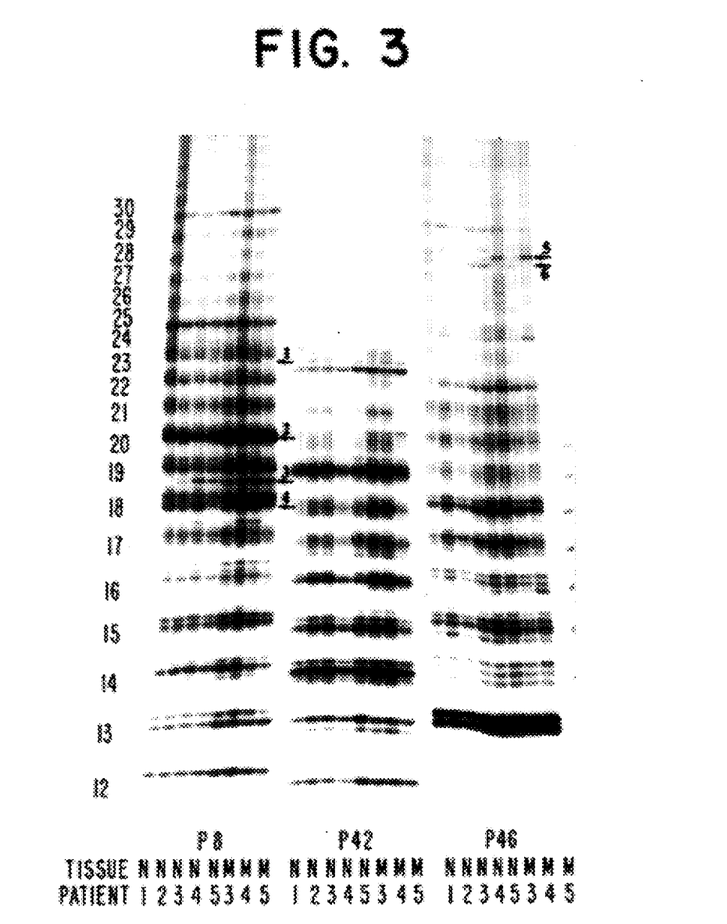
FIG. 3 Comparison of patterns for poly(A)$^+$RNAs purified from normal myometrium (N, patients 1 and 2), myometrium, surrounding myomas (N, patients 3, 4 and 5) and myomas (M, patients 3 and 5) from human uteri using primers P8, P42, P46.

We have tried to observe individual-specific and myoma-specific differences in poly(A)$^+$RNA spectra from two normal (without pathology) uteri and three pathological uterine (myometrium and myoma) samples. Six primers out of 30 showed individual-specific differences and only 2 primers could detect myoma-specific differences (FIG. 3). The P8 primer identifies individual-specific changes such as the appearance of new RNAs (band 1, patient 4) or changes in the content of individual RNAs (band 2, patient 5; band 4, patient 3). Primer P8 also reveals an increased content (about 3-5 fold) of individual RNA (band 3) both in myometrium and in myoma in all 3 cases (patients 3, 4 and 5) compared to the normal uterine samples (patients 1, 2). Also primer P46 reveals the increasing intensity of band 6 and decreasing intensity of band 5 for all three myomas (patients 3, 4 and 5) compared to normal myometrium (patients 1, 2) and myometrium surrounding myomas (patients 3, 4 and 5). Based on this data we can arrive at the following conclusions. Firstly, the number of myoma-specific differences doesn't exceed the quantity of individual-specific differences. Secondly, myoma-specific differences in gene expression are characterized by 3-5 fold changes in individual RNA levels (e.g. primer P8, band 3; primer P46, bands 5 and 6), but not with the appearance or disappearance of new RNAs. It should be noted that the 3-5 fold changes in individual RNA levels could be underestimated due to the possible coincidence of mobilities of different terminated oligonucleotides. It is interesting that two-dimensional gel electrophoretic analysis of neoplastic transformation also reveals changes in the relative proportions of proteins normally synthesized by somatic cells rather than in the appearance of new proteins (3, 30, 31). Thirdly, this method of analysis of poly(A)$^+$RNA spectra cannot, as yet, reveal the small changes in the low-abundance individual RNAs (0.01-0.1%). The main reason for this, is the high "background" contributed from bands which remain constant during the course of transformation. Weak signals from differentially expressed genes cannot be detected above this "background" without finding a way to reduce it. One way to overcome the "background" problem will be to use poly(A)$^+$RNA fractions enriched for differentially expressed RNAs (5).

Example 4

Differentiation of F9 embryonal carcinoma cells

To demonstrate further the field of application of our poly(A)$^+$RNA pattern method to cell biology, we chose as another model the differentiation of mouse F9 cells.

F9 embryonal carcinoma cells (derived from a mouse testicular teratocarcinoma) do not undergo significant spontaneous differentiation, but can be induced to differentiate to parental endodermic cells by treatment with retinoic acid and dibutyryl cAMP (16). Changes in the cellular phenotype, which occur in vitro after 2-3 days of such treatment, are well defined by coordinate changes in expression of specific marker genes: e.g. plasminogen activator, collagen type IV, laminin B1 and B2 chains, cytokeratin EndoA and EndoB, Sparc, H-2 class 1 and beta$_2$-microglobulin (32-34). Regulation of expression of these genes mainly occurs at the transcriptional level and is accompanied by significant differences in the steady state levels of individual mRNAs (32-34).

Figure 4:
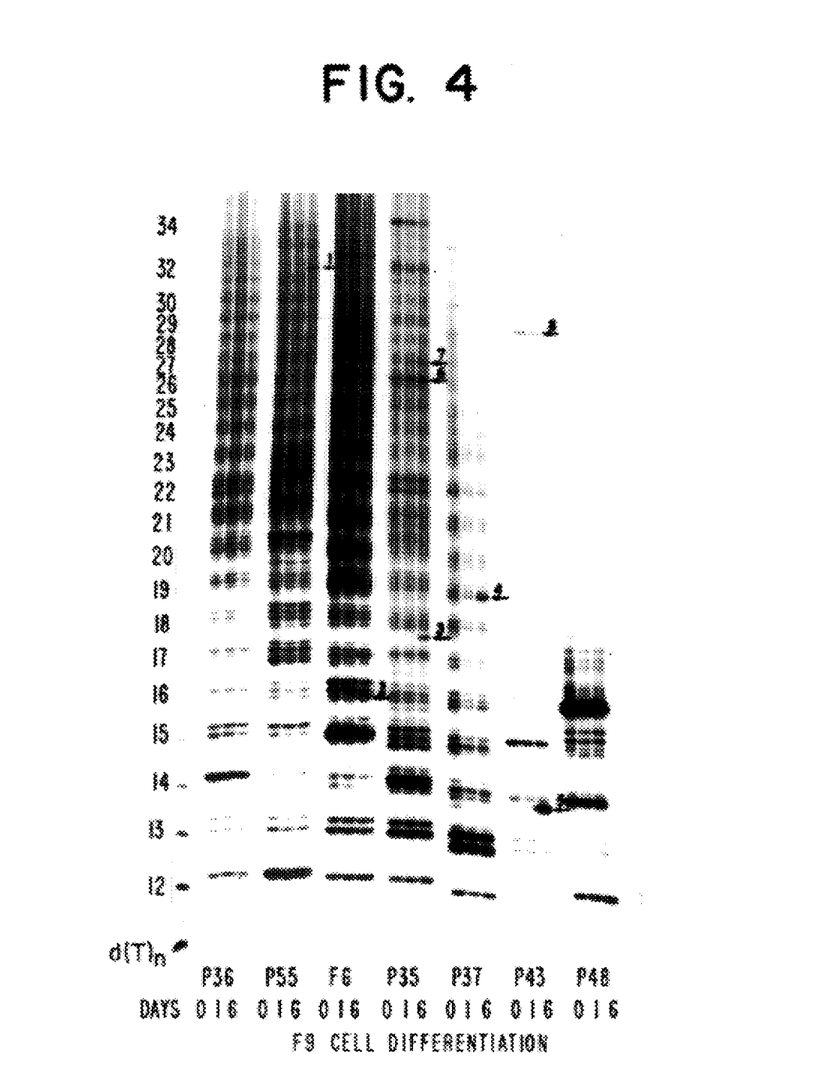
FIG. 4 Changes in cDNA synthesis product patterns synthesized by M-MLV reverse transcriptase using poly(A)$^+$RNA from non-differentiated (0) or F9 cells, treated with retinoic acid and dibutyryl cAMP for 1 day (1) or 6 days (6) using primers P36, P55, F6, P35, P37, P43, P48.

We have attempted to identify changes in individual mRNA content by analysing poly(A)$^+$RNA patterns, purified from non-differentiated F9 cells (FIG. 4, lane 1, for all primers) and F9 cells treated with a mixture of retinoic acid and dibutyryl cAMP for 1 day (FIG. 4, lane 2) and 6 days (FIG. 4, lane 3). Out of 30 primers, at least 8 identified 10 separate differentially expressed mRNAs (FIG. 4). Primers P55, P35, P37 and P43 revealed 4 individual mRNAs (bands 1, 3, 4, 5) induced at least 3 fold after 6 days of differentiation. Primer F6 (band 2, 6 days of differentiation) provides an example of a small (less than 2 fold) change in mRNA content, although the actual change may be much higher, taking into account the high "background" in band 2 (0, 1 day of differentiation). Primers P36 and P48 did not reveal any differences in the poly(A)$^+$RNA pattern during F9 cell differentiation. Table 1B shows the results of sequencing the differentially represented bands 1, 3, 4, 5 and the bands 6, 7, 8 which did not change their level of expression. As in the case of fetal liver (table 1A, bands 9, 11, 12, 13) we found several examples of unclear sequencing (table 1B, bands 4, 6, 7) and misincorporation (bands 1, 3). Searching of complementary mRNA target sites in the GenBank database revealed that band 1 corresponds to mouse α1-collagen type IV mRNA, band 3—mouse T-complex associated testis-expressed peptide (Tctc 1) mRNA, band 5—mouse laminin A mRNA and bands 6, 8—mouse 28S rRNA. The sequences of bands 4 and 7 did not correspond to any complementary sites amoung genes/mRNAs accumulated in the GenBank database.

As the length of band 5 was too short (12 nucleotides) for searching complementary sequences in the GenBank database, we "extended" this band by deliberately adding 0.2 μM of dTTP, in addition to ddUTP (5AA-Fam) and sequenced the band terminated at the second T, which was 3 nucleotides longer. This resulted in identification of the laminin A mRNA sequence (table 1B, band 5). Among the detected differentially expressed mRNAs, mouse α1-collagen type IV mRNA and laminin A mRNA are well known markers of differentiated F9 cells (32), and Tctc 1 mRNA (35) is a new marker for F9 cell differentiation.

Example 5

Use of cDNA as a template for RNA fingerprinting

Figure 5:
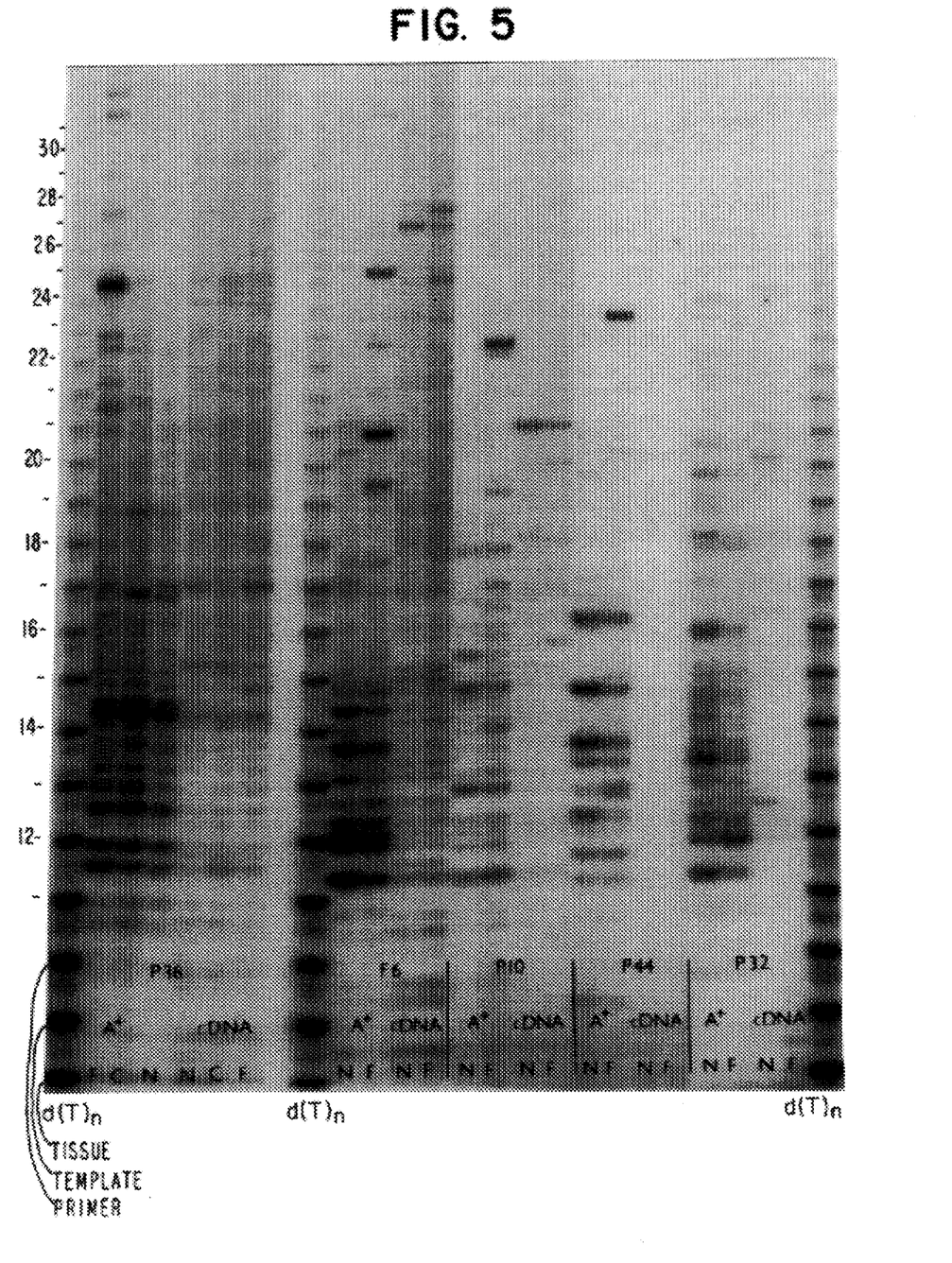
FIG. 5 Comparison of patterns for normal (N), cirrhotic (C) and fetal (F) human liver poly(A)$^+$RNAs (A$^+$) or cDNAs using primers P36, F6, P10, P44, P32.

To investigate the possibility of using cDNA, instead of poly(A)⁺RNA, as a template in RNA fingerprinting, single-stranded cDNAs were synthesised from normal, cirrhotic and fetal human liver poly(A)⁺ RNAs, using primer F6 to initiate synthesis. The resulting cDNAs were then compared with their corresponding poly(A)⁺ RNAs for their abilities to act as templates in the fingerprinting procedure, using five different oligonucleotide primers (P36, F6, P10, P44 and P32). The results, presented in FIG. 5, showed that four of the primers used (P36, F6, P10 and P32) show clear quantitative and qualitative differences in the fingerprinting patterns for normal and fetal liver cDNA.

In general the banding pattern obtained using the cDNA templates was different, and contained less bands per lane, compared with that observed using the corresponding poly (A)⁺RNA template. The main reason for this, results from the use of the F6 primer to generate the single-stranded cDNA templates. This primer only initiates synthesis on approximately 30% of the RNA templates present, producing an F6 "subset" of first strand cDNA templates. cDNA "subsets" of differing complexity, ranging from 2% (primer P32) to 100% (oligo d(T)$_{12-18}$), can be generated for use in the fingerprinting process, by employing alternative primers for synthesizing the first strand cDNA template. The use of different primers for generating the second strand fingerprinting pattern would then allow a more detailed analysis of differences already revealed using the corresponding poly (A)⁺RNA sample. The possibility then exists to use PCR amplification for subsequent cloning/sequencing using any combination of first and second strand cDNA synthesis primers which had revealed differentially expressed sequences.

Example 6

Use of [$^{32}$P]-labelled terminator ddATP for RNA fingerprinting

The use of [$^{32}$P]-labelled terminator ddATP ("Amersham"), instead of 5'-[$^{32}$P]-labelled primers, to label cDNA synthesis products was investigated, since this could offer several advantages to the RNA fingerprinting procedure. For example, use of a labelled terminator nucleotide would avoid the need for many separate labelling reactions for each primer used (up to 30). The need for a phosphodiesterase digestion step could also be eliminated since, by using a labelled terminator, only $^{32}$P-labelled terminated oligonucleotides would be visible on the resulting autoradiograph.

Figure 6:
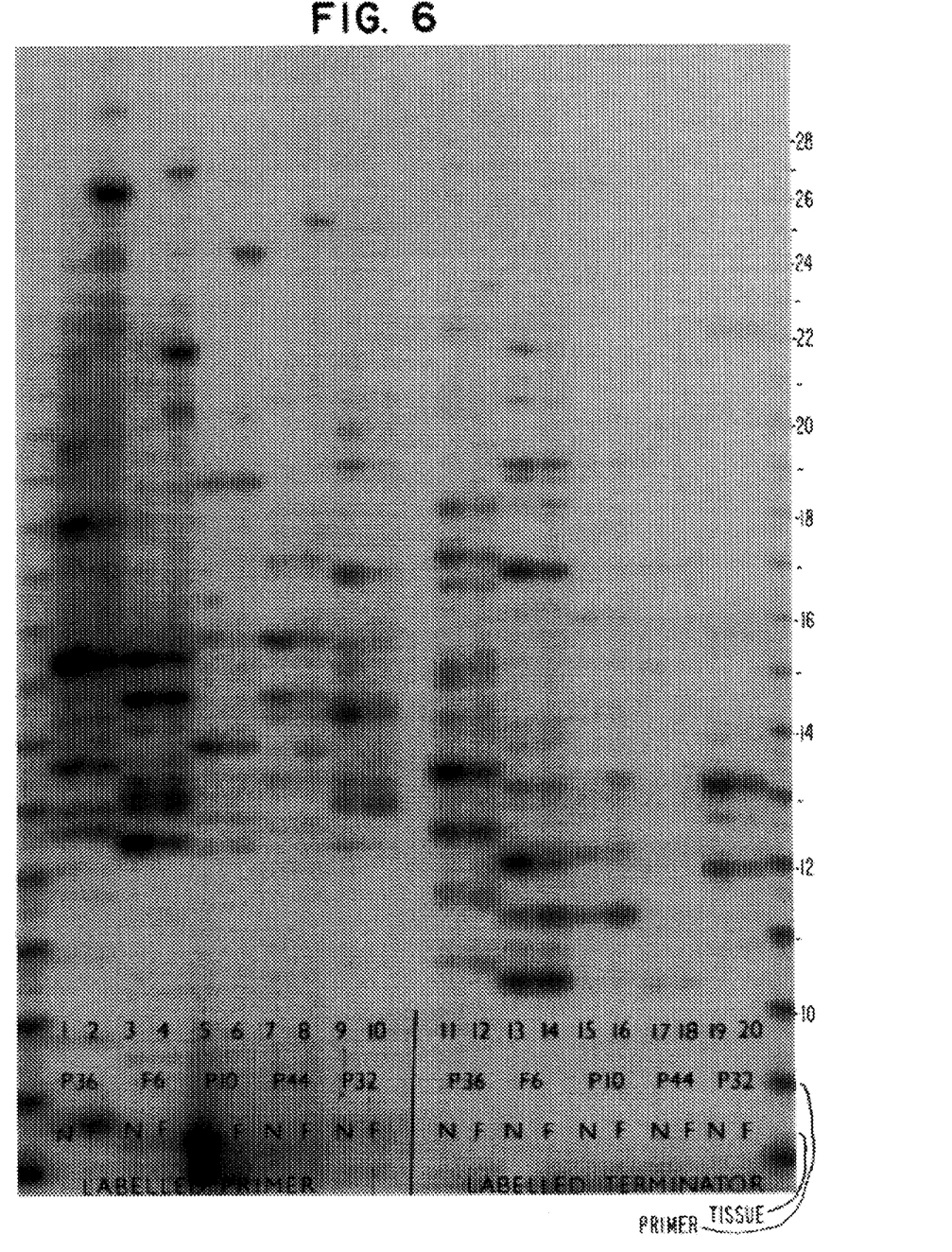
FIG. 6 Comparison of patterns for 5'-[$^{32}$P]-labelled primers with ddUTP (5AA-Bio) (1–10) or [$^{32}$P]ddATP (11–20) using normal (N) or fetal (F) human liver poly(A)$^+$RNAs and primers P36, F6, P10, P44, P32.

FIG. 6 shows a comparison of the poly(A)⁺RNA patterns obtained with normal (N) or fetal (F) Human liver poly(A) ⁺RNAs, using either [$^{32}$P]-labelled primers (lanes 1-10) or [$^{32}$P]-labelled terminator ddATP (lanes 11-20). Since different terminators (i.e. ddUTP (5AA-Bio) or [$^{32}$P]-ddATP respectively) were used for this comparison, the RNA fingerprints, obtained using the two different labelling methods, are different when comparing corresponding lanes (c.f. lanes 1 and 11, 2 and 12). More detailed information about differentially expressed bands could be obtained for any particular primer, by using other labelled terminators (e.g. ddUTP, ddCTP or ddGTP) in separate reactions. Some differentially expressed bands may not be identified using only one terminator, particularly if they co-migrate with other bands whose level of expression remain constant between the two poly(A)⁺RNA samples (especially for bands in the 10-12 nucleotide zone of the gel, c.f. lanes 3 and 13, 4 and 14).

Under the conditions used in these studies (10 μM of [$^{32}$P]-labelled ddATP, 5 μCi per reaction) the sensitivity of band intensities on the resulting RNA fingerprint was 2-3 fold lower compared with the results using the [$^{32}$P]-labelled primer. This sensitivity is still sufficient, however, to provide a complete poly(A)⁺RNA profile, using all 30 available primers, from as little as 2-3 μg of any poly(A)⁺RNA.

CONCLUSIONS

The method of analysis of poly(A)⁺RNA patterns according to the invention is a valuable technique, expected to be useful for monitoring changes in gene activity, as an alternative to high resolution 2-dimensional gel electrophoresis of cellular proteins. This poly(A)⁺RNA pattern method may be successfully applied to the investigation of tissue-type specific regulation of gene expression (and its relationships with primary structure of individual mRNAs) and in searching for differentially expressed genes during the processes of differentiation, transformation, cell cycle regulation and mutagenesis in cells cultivated in vitro. Further improvements of the poly(A)⁺RNA pattern method described are likely to be directed towards three unresolved issues. Firstly, modifications to the gel separation system will help to maximise the separation of oligos of equal length but with different nucleotide sequences. A second aim will be to reduce the "background" (i.e. those electrophoretic bands coinciding with differentially expressed mRNA bands). Thirdly, a suitable approach for cloning the differentially expressed genes, on the basis of information obtained from analysis of the RNA fingerprint, will be investigated.

TABLE 1

Sequence of the individual bands and identification of RNAs in GenBank database.

| Band No | Sequence* of Primer-synth.cDNA (5'→3') RNA(s) target site (3'←5') | Name of Primer/RNA(s) | GenBank database references (5'- -end RNA target site position) |
|---|---|---|---|
| A. Normal, cirrhotic and fetal livers (FIG. 2) | | | |
| 8 | TGTGGCAGGggg t<br>Numerous | F6<br>6 mRNAs | |

TABLE 1-continued

Sequence of the individual bands and identification of RNAs in GenBank database.

| Band No | Sequence* of Primer-synth.cDNA (5'→3') RNA(s) target site (3'←5') | Name of Primer/RNA(s) | GenBank database references (5'--end RNA target site position) |
|---|---|---|---|
| 9 |       g<br>TGTGGCAGG ggaacggct<br>            a<br>CGCCCGTCCTCCTTGCCGA | P6<br>α2-globin | HUMAGL1(837) |
| 10 | TGT-GGCAGGa gacagcaccat<br>ACAGCCGTCCTCTGTCGTGGTA | P6<br>α1-globin<br>α2-globin | HUMAGL1(137) |
| 11 |       g<br>TGCTGGCAGg ggaacggct<br>          a<br>TCGCCCGTCCTCCTTGCCGA | P41<br>α2-globin | HUMAGL1(837) |
| 12 |       g<br>TGCTGGCAGg gacagcaccat<br>          a<br>ACAGCCGTCCTCTGTCGTGGTA | P41<br>α1-globin<br>α2-globin | HUMAGL1(137) |
| 13 |       g<br>TGCTGGCAG ggcagaggacaggt<br>      a<br>ACTACCGTCTCCGTCTCCTGTCCA | P41<br>G$_\gamma$-globin<br>A$_\gamma$-globin | HUMBGG(162)<br>HUMHBGAB(444) |
| 14 | TGCTGGCAGgggacagcaccacggt<br>None | P41<br>None | |
| 15 | TGCTGGCAGgggggggcagcgcaggggct<br>None | P41<br>None | |
| 16 | TGCTGGTGGggat<br>CCGACCACCCCTA | P36<br>Cytochrome P450<br>Cystein proteinase inhibitor | HUMCYPC219 (1088)<br>HUMINCP(1280) |
| 17 | TGCTGGTGGggaaggacaggaacat<br>ACCACCACCCCTTCCTGTCCTTGTA | P36<br>α1-globin<br>α2-globin | HUMGL1(350) |
| 18 | TGCTGGTGGgcagagcgcgggcaggcgt<br>GCGACCACCCGTCTCGCGCCCGTCCGCA | P36<br>Insulin-like<br>growth factor II | HUMIGF2FP (269) |

B. F9 cell differentiation (FIG. 4)

| | | | |
|---|---|---|---|
| 1 | TGCTGGGTGgggagcgcagagccccggcgt<br>TCGACCCACGCCTCGCGTCTCGGGGCCGCA | P36<br>α1(α2)-collagen type IV | MUSCOL4A(403) |
| 3 | TGCTGGCGGacagcct<br>GCGACCGCCCGTCGGA | P35<br>T-complex testis expressed peptide | MUSTCTEI(1465) |
| 4 |       g<br>TGCTGACGGg ggaacggct<br>          a<br>None | P37<br>None | |
| 5 | TGCTGACGGc at ( agt )$^b$<br>GCGACTGCCGTA( TCA) | P43<br>Laminin A | MUSLASMAR1(552) |
| 6 |       gg<br>TGCTGGCGGg agacgggccggt<br>      aa<br>CGCGCCGCCCGCTCTGCCCGGCCA | P35<br>28S rRNA | MUSRRM(1277) |

TABLE 1-continued

Sequence of the individual bands and identification of RNAs in GenBank database.

| Band No | Sequence[a] of Primer-synth.cDNA (5'→3') RNA(s) target site (3'←5') | Name of Primer/RNA(s) | GenBank database references (5'--end RNA target site position) |
|---|---|---|---|
| 7 | a<br>TGCTGGCGGg c g g c g a g a c g g c g t<br>                g<br>None | P35<br>None | |
| 8 | *TGCT*GACGGgc g a g a g g g c g g c c c c c t<br>*TGC*ACTGCCCGCTCTCCCGCCGGGGGA | P43<br>28S rRNA | MUSRRM(4554) |

[a]Upper case letters in upper row show sequence of the primer used, mismatched bases are printed in italic and underlined. Synthesized cDNA sequence is printed in lower case letters. Uncertainties in sequencing are marked by two bases at one position and underlined.
[b]Brackets mark the sequence of band 5 after extension in the presence of 0.2 μM dTTP.

REFERENCES

1. Lewin B. (1980) Gene expression, 2, Eucaryotic genomes. New York, Wiley, 694–727.

2. Lewin B. (1985) Genes. New York, Wiley, 230–236.

3. Celis J. E., Bravo R. eds. (1984) Two-Dimensional Gel Electrophoresis of Proteins. Orlando, Acad. Pres, 4–36, 260–354, 445–476.

4. Celis J. E. Rasmussen H. H., Leffers H., Madsen P., Honore B., Gesser B., Bejgaard K., Vandekerckhove J. (1991) Faseb J., 5, 2200–2208.

5. Rubenstein J. L. R., Brice A. E. J., Ciaranello R. D., Denney D., Porteus M. H. Usdin T. B. (1990) Nucleic Acids Res., 18, 4833–4842.

6. Duguid J. R., Dinauer M. C. (1990) Nucleic Acids Res., 18, 2789–2792.

7. Hedrick S. U., Kohen E. L, Nielson E. H. and Devis, M. M., (1984) Nature 308, 149–153.

8. Timblin C., Battey J., and Kuehl W. M. (1990) Nucleic Acids Res., 18, 1587–1593.

9. Patent: WO 91/14001: A process for distinguishing nucleic acids on the basis of nucleotide differences—Published 19 Sep. 1991.

10. Welsh J., Chada K., Dalal S. S., Cheng R., Ralph D. and McClelland M. (1992) Nucleic Acids Res., 20, 4965–4970.

11. Liang P. and Pardee A. B. (1992) Science 257, 967–971.

12. Ellsworth D. L., Rettenhouse K. D. and Honeyhutt R. L. (1993) Biotechniques, 14, 214–217.

13. Stahl D. A., Krupp G. and Stackebrandt E. (1989) in: Nucleic Acid Sequencing—A practical Approach (Howe C. J. and Ward E. S. eds) pp.171–177 IRL press, Oxford.

14. Sambrook J., Fritsh E. F., Maniatis T. (1989) Molecular cloning. CSH, CSH Press, 10.6–10.16.

15. Fujii S. (1983) Acta Obstet Gynec. Japan 35, 1166–1174.

16. Strickland S., Mahdavi V. (1978) Cell, 15, 393–403.

17. Sambrook J., Fritsh E. F., Maniatis T. (1988) Molecular cloning, CSH, CSH Press, 7.18–7.42.

18. Aleksandrova L. A., Lukin M. A., Rozovskaya T. A., Atrazhev A. M., Kukhanova M. K., Krayevsky A. A. (1990) Mol. Biol. (Moscow) 24, 1100–1108.

19. Williamson J. R. and Celander D. W. (1990) Nucleic Acids Res. 18, 379.

20. Sverdlov E. D. and Kalinina, N. F. (1983) Bioorg. Chem. (Moscow). 9, 1696–1697.

21. Devereux J., Haeberli, P. and Smithies O. (1984) Nucleic Acids Res. 12, 387–395.

22. Diachenko L. B., Chenchik A. A., Lukin M. A., Aleksondrova L. A., Krayevsky A. A., Beabealashvilli R. Sh. (1991) Mol. Biol. (Moscow), in press.

23. Bowling J. M., Brunner K. L., Charik J. L., Tibbetts C. (1991) Nucleic Acids Res., 19, 3089–3097.

24. Sieminick D. R., Sliykton I. J., (1990) Gene, 96, 121–124.

25. Beabealashvilli R. Sh., Chenchik A. A., Diachenko L. B. (1991) Mol. Biol. (Moscow), in press.

26. Chenchik, A. A. Diachenko, L. B. and Beabeashlashville R. Sh. (1992) Mol Biol (Moscow). 26, 1189–1194.

27. Bissel D. M., Roll F. J. (1989) Hepathology, 2nd ed. Philadelphia, W. Saunders Co., 4214–444.

28. Higgs D. R., Vickers M. A., Wilkie A. O. M., Pretorius I. M. and Weatherall, D. J. (1989) Blood. 73, 1081–1104.

29. Gray A., Tam A. W., Dull T. J. Hayflick J., Pintar J., Cavenee W. K. and Ullrich A. (1987) DNA. 6, 283–295.

30. Celis J. E., Bravo R. eds (1983) Gene expression in normal and transformed cells. New York, Plenum, 291–314.

31. Thorsrud A. K., Vath M. H., Jellum E. (1982) Clin. Chem., 28, 884–889.

32. Goodfellow P. N. (1984) Cell Differentiation, 15, 257–267.

33. Rickles R. J., Darrow A. L., Strickland S. (1988) J. Biol. Chem., 263, 1563–1569.

34. Mason I. J., Taylor A., Williams J. G., Sage H., Hogan B. L. M. (1986) EMBO J., 5, 1465–1472.

35. Sarvetnick N., Tsai J. Y., Fox H., Pilder S. H., Silver L. M. (1989) Immunogenetics, 30, 39–41.

We claim:

1. A method of producing a fingerprint of a eukaryotic poly(A)+ RNA preparation comprising;

adding to the poly(A)+ RNA preparation or to a single-stranded cDNA preparation derived therefrom at least one oligonucleotide primer and four different nucleotides, wherein three of the nucleotides permit elongation and one of the nucleotides is a chain terminator;

synthesizing cDNA products from said RNA preparation or DNA products from said single-stranded cDNA preparation; and separating said cDNA products or DNA products to produce a fingerprint.

2. The method according to claim 1, wherein the oligonucleotide primer(s) is(are) 8 to 10 nucleotides in length.

3. The method according to claim 1, wherein the number of primers and nucleotide sequence of the primers are chosen to provide a sufficiently detailed fingerprint to allow the fingerprints obtained from different poly(A)+ RNA or cDNA preparations to be distinguished from each other.

4. The method according to claim 1, wherein the chain terminating nucleotide is any modified nucleotide triphosphate possessing chain terminating properties when used with any DNA polymerase.

5. The method according to claim 1, wherein the chain terminating nucleotide is dideoxyuridine triphosphate.

6. The method according to claim 1, wherein the chain terminating nucleotide is dideoxyuridine triphosphate containing either a biotin or a fluorescein group at the 5-position of the pyrimidine ring.

7. The method according to claim 1, wherein the separating of the cDNA products or DNA products is carried out by electrophoresis.

8. The method according to claim 1, wherein the primer(s) is(are) labeled with a detectable label.

9. The method according to claim 1, wherein the chain terminating nucleotide is labeled with a detectable label.

10. The method according to claim 1, wherein said poly(A)+ RNA preparation is isolated from a tissue selected from the group consisting of normal human tissues, fetal tissues, cirrhotic human liver tissues, human cancerous tissues, uterine myoma tissue, and mouse testicular teratocarcinoma cells.

11. A method for comparing the poly(A)+ RNA in two or more cell populations comprising, producing a fingerprint of a poly(A)+ preparation for each cell population by the method according to claim 1, and visually or otherwise comparing the separated cDNA products or DNA products in the respective fingerprints.

12. The method according to claim 11, wherein one or more of the separated cDNA products or DNA products are further compared by isolating and sequencing the products.

* * * * *